(12) United States Patent
Rossier et al.

(10) Patent No.: US 7,390,389 B2
(45) Date of Patent: Jun. 24, 2008

(54) APPARATUS AND METHOD FOR SEPARATING AN ANALYTE

(75) Inventors: Joel Stephane Rossier, Vionnaz (CH); Frédéric Reymond, La Conversion (CH); Philippe Michel, Collombey (CH)

(73) Assignee: Diagnoswiss S.A., Monthey (CH)

(*) Notice: Subject to any disclaimer, the term of this patent is extended or adjusted under 35 U.S.C. 154(b) by 891 days.

(21) Appl. No.: 10/486,181

(22) PCT Filed: Aug. 30, 2002

(86) PCT No.: PCT/EP02/10369

§ 371 (c)(1), (2), (4) Date: Feb. 6, 2004

(87) PCT Pub. No.: WO03/019172

PCT Pub. Date: Mar. 6, 2003

(65) Prior Publication Data

US 2004/0231986 A1    Nov. 25, 2004

(30) Foreign Application Priority Data

Aug. 31, 2001    (GB)    .................................. 0121189.5

(51) Int. Cl.
*G01N 27/447* (2006.01)
*G01N 27/453* (2006.01)

(52) U.S. Cl. ........................................ 204/548; 204/644
(58) Field of Classification Search ................. 204/548, 204/644

See application file for complete search history.

(56) References Cited

U.S. PATENT DOCUMENTS

| | | | |
|---|---|---|---|
| 2,815,320 A | 12/1957 | Kollsman | |
| 3,719,580 A | 3/1973 | Roberts et al. | ............... 204/299 |
| 3,888,758 A | 6/1975 | Saeed | .......................... 204/299 |
| 4,148,703 A | 4/1979 | Trop et al. | |
| 4,362,612 A | 12/1982 | Bier | |
| 4,971,670 A | 11/1990 | Faupel et al. | |

(Continued)

FOREIGN PATENT DOCUMENTS

DE    2051715 A    4/1972

(Continued)

OTHER PUBLICATIONS

Righetti et al. "Protein purification in multicompartment electrolyzers with isoelectric membranes", Journal of Chromatography B, 1997, vol. 699, pp. 105-115.*

(Continued)

*Primary Examiner*—Kaj K Olsen
(74) *Attorney, Agent, or Firm*—Howson & Howson LLP

(57) ABSTRACT

The present invention relates to an apparatus and method for the separation and purification of charged and neutral compounds in an analyte solution by electrophoretic means using a plurality of compartments (1) to contain the analyte solution, an chemical buffering system (2) to fix a pH value or a pH gradient in its portion(s) contacting the analyte solution and an electrical field imposed by electrical means (4) disposed in at least two of said compartments. This invention allows one to differentially separate charged and neutral compounds, to extract the migrating compounds from the chemical buffering system (2), to recover the purified compounds mainly in solution and to collect them in the various compartments (4), preferably at various pI.

36 Claims, 14 Drawing Sheets

U.S. PATENT DOCUMENTS

| | | | |
|---|---|---|---|
| 5,082,548 A | | 1/1992 | Faupel et al. |
| 5,114,555 A | | 5/1992 | Stimpson |
| 5,126,022 A | * | 6/1992 | Soane et al. ............... 204/458 |
| 5,149,418 A | | 9/1992 | Flesher .................. 204/299 R |
| 5,540,826 A | | 7/1996 | Bier et al. .................. 204/610 |
| 5,773,645 A | | 6/1998 | Hochstrasser |
| 5,834,272 A | * | 11/1998 | Righetti ...................... 435/174 |
| 6,007,865 A | | 12/1999 | Cerami et al. |
| 6,013,165 A | | 1/2000 | Wiktorowicz et al. |
| 6,328,869 B1 | * | 12/2001 | Ogle ........................... 204/600 |
| 6,638,408 B1 | * | 10/2003 | Speicher et al. ............ 204/458 |
| 6,706,162 B1 | | 3/2004 | Voss et al. |
| 2003/0104449 A1 | | 6/2003 | Faupel et al. .................. 435/6 |

FOREIGN PATENT DOCUMENTS

| | | |
|---|---|---|
| EP | 0173081 A1 | 3/1986 |
| EP | 0457526 A2 | 11/1991 |
| EP | 0776700 A1 | 6/1997 |
| GB | 1422118 | 1/1976 |
| WO | WO 00/74850 A2 | 12/2000 |
| WO | WO 01/68225 A1 | 9/2001 |
| WO | WO 01/75432 A2 | 10/2001 |
| WO | WO 01/86279 A1 | 11/2001 |

OTHER PUBLICATIONS

Righetti et al. "Preparative protein purification in a multi-compartment electrolyser with immobiline membranes", Journal of Chromatography, 1989, vol. 475, pp. 293-309.*

Zuo et al. "A method for Global Analysis of Complex Proteomes Using Sample Prefractionation by Solution Isoelectrofocusing Prior to Two-Dimensional Electrophoresis", Sep. 10, 2000, Analytical Biochemistry vol. 284, pp. 266-278.*

Rylatt et al. "Electrophoretic transfer of proteins across polyacrylamide membranes", 1999, Journal of Chromatography A, vol. 865, pp. 145-153.*

Righetti et al. "Preparative electrophoresis with and without immobilized pH gradients", 1992, Advances in electrophoresis, vol. 5, pp. 159-200.*

G. Kemp, "Capillary Electrophoresis: a Versatile Family of Analytical Techniques", Biotechnol. Appl. Biochem., No. 27, pp. 9-17, Jun. 1998.

Koegler et al., "Focusing Proteins in an Electric Field Gradient", Journal of Chromatography A, vol. 229, pp. 229-236, Mar. 1996.

* cited by examiner

A

B

A

B

C

APPARATUS AND METHOD FOR SEPARATING AN ANALYTE

This application is a 371 National Stage Entry of PCT/EP02/10369, filed on Aug. 30 2002.

BACKGROUND OF THE INVENTION

In the expending field of proteomics, complex biological samples that can contain up to 30,000 different proteins have to be separated and analyzed.

Up to now, two-dimensional (2D)-gel electrophoresis has been the technique of choice to identify and classify proteins according to their isoelectric point (pI) and mass (Wilkins, M. R. et al., Proteome Research: New Frontiers in Functional Genomics; Springer, 1997). Indeed, with 2D-gel electrophoresis, proteins are separated first by an isoelectric focusing (IEF) step according to their pI. Secondly, proteins are separated as a function of their molecular mass by a polyacrylamide gel electrophoresis (PAGE) step. The proteins can thus be classified in databases according to their pI and mass.

However, despite its extraordinary resolving power, it appears that 2D-gel electrophoresis has reached a plateau in the number of proteins that can be separated and detected in a single map. Moreover, with 2D-gel electrophoresis, only protein separation and classification according to pI and mass can be achieved. Further analysis of the proteins is required in order to obtain more specific information, such as for example peptide composition or biological activity. For this purpose, the proteins have to be extracted out of the gel matrix and analyzed with the appropriate technique. Extraction procedures such as blotting or spot cutting are time consuming and/or risky for protein recovery and activity.

Once a protein has been extracted, the most powerful analytical technique is mass spectrometry (MS), which allows one to analyze peptide composition. However, for MS analysis, the purity of the samples is critical and they generally have to be treated before measurements, which complicates the procedure. Indeed, if the sample contains salts or other impurities, disadvantages can arise for MS analysis. Thus, a sample with a high concentration of salt needs to be desalted by means such as a dialysis procedure before MS analysis. Moreover, the extraction method is not favorable for MS analysis since it leads to a high concentration of undesired compounds in the recovered sample. Some methods to avoid undesired compounds in the samples have been developed. For example, a direct laser desorption technique from the 2D-gel was described by Ogorzalek Loo R. R. et al. (Analytical Chemistry, 1996, 68, 1910-1917) and an electroblotted 2D-gel was developed by Eckerskorn C. et al. (Analytical Chemistry, 1997, 69, 2888-2892). So the major problem with 2D gel-electrophoresis is that the compounds to be analyzed are trapped within a gel and must be extracted and purified before further analyses.

Another efficient technique to separate complex biological samples is isoelectric separation as for example isoelectric focusing (IEF). There are two major types of IEF devices: free flowing buffered systems and immobilized buffered systems.

The free flowing systems (Soulet, N. et al., Electrophoresis, 1998, 19, 1294-1299; Fuh, C. B. and Giddings, J. C., Separation Science and Technology, 1997, 32, 2945-2967, Bier, U.S. Pat. No. 5,540,826) are based on the use of a buffer (carrier ampholytes or isoelectric buffers). In this case, the major disadvantage is that the final separated fractions contain a certain amount of undesired buffering species or ampholytes. This is a problem since these additional compounds have to be removed before further analyses.

In the case of the immobilized buffering systems, the major disadvantage is that the final separated fractions are trapped in a gel or a membrane, which complicates further analyses. However, a "segmented immobilized pH gradients" device based on the use of multiple compartments separated by immobiline isoelectric membranes was developed by Righetti et al. (Journal of Chromatography, 1989, 475, 293-309). The advantage of this technique is that proteins are recovered in an ampholyte-free solution. However, this method requires the use of multiple compartments, multiple immobilized membranes and segmented pH gradients.

Therefore, the development of new high throughput techniques that allow the separation of complex biological samples and the direct recovery in solution of the compounds to analyze is required. These techniques should minimize separation times, be easy to use and result in a high degree of purity.

Recently, a novel method and apparatus was developed and described by Ros et al. (WO 01/86279). In this case, it is possible to purify compounds that are globally neutral from charged species in a sample which does not need to be buffered. The principle of this method is to flow proteins under an immobilized pH gradient (IPG) gel through which an electric field is applied perpendicular to the direction of the flow. Thanks to the buffering capacity of the IPG gel, proteins in solution close to the gel are extracted with respect to their isoelectric point. Only the proteins with a pI close to the pH of the IPG gel stay in the flowing solution. This technique can be used as a prefractionation step before further analysis, and can also be used as a gel loading method. This technique provides a very high separation rate since the molecules migrate in solution and not in a gel as in IEF systems. The device developed for this OffGel®) electrophoresis is made of:
- a chamber above which an immobilized chemical buffering system (e.g. an IPG gl) is inserted, to close the chamber and buffer it at the desired pH range.
- two platinum electrodes (placed at each extremity of the device) for producing an electrical current along the IPG gel, above which apertures are made to serve as cathodic and respectively anodic reservoirs and to let the possible gas produced during the purification escape out of the device, and
- optionally, an inlet and an outlet, connected via tubing to a peristaltic pump to recirculate the sample.

In this case, the potential difference is only applied through at least a portion of the chemical buffering system. This electrophoresis technique offers extraordinary potentialities and allows the direct recovery of the compounds of interest in solution. However, the device is not very convenient for modem life sciences such as proteomics, which requires high throughput techniques, with short purification time and optimized compound recovery. Furthermore, the strong drawback of Off-Gel electrophoresis is that only components of pI=pH of the gel in contact with the chamber are recovered in solution. It is indeed clear that any other proteins with pI close to the pH of the gel will migrate inside the gel and will be lost for further analysis. Furthermore, preconcentration of sample is probably difficult to realize with Off-Gel electrophoresis, which is one of the bottlenecks of proteomics for analysis of low abundant proteins.

Various systems have been developed for electrophoretic separation purposes. Even though many of them do use either a multi-compartment device or a gel- or membrane-based support (as e.g. the apparatuses described in EP 0776700, GB1422118, EP 0173081, U.S. Pat. No. 5149418 or U.S. Pat. No. 3719580), they refer to conventional electrophoresis separation systems. Indeed, these systems are based on the classical principles of electrophoretic migration of molecules in an electrical field, and they are generally devoted to the separation of molecules according to their size or mass as as widely used for the separation of DNA molecules or fragments. Indeed, such compounds do not have amphoteric properties (in contrast to e.g. proteins) and hence they always exhibit the same charge during the separation. These electrophoretic separation systems therefore do not allow one to separate compounds according to their respective isoelectric point. Indeed, the gels or membranes used in these systems do not comprise any buffering means to fix the pH, and these electrophoretic separation systems are thus fundamentally different from the aforementioned IEF apparatuses, since they are based on totally different separation principles.

SUMMARY OF THE INVENTION

One aim of the present invention is to improve OffGel electrophoresis and to adapt it to a high throughput format directly compatible with the means and instruments that are generally used in life sciences such as proteomics. A particular aim is to improve the recovery of the compounds of interest by improving the distribution of the current lines.

Another aim of the present invention is to provide a high throughput device and method to separate charged and neutral compounds and to recover neutral compounds of interest in a solution which does not need to be buffered.

The present invention provides an apparatus for separating an analyte from a solution and a method for separating an analyte from a solution. A (multi)compartment set-up and a special disposition of electrical means are used. A chemical buffering system (e.g. ampholytes or an immobiline gel) is adjacent a plurality of solution reservoirs formed by the compartments and serves to define a desired pH value or pH gradient in its portion contacting the analyte solution. In one aspect of the invention, the compartments are separated by a direct fluidic connection characterized in that it prevents natural convection but allows difftision and migration between two adjacent compartments. By application of an electrical field across the various compartments, the charged molecules are forced to migrate until they reach the locus corresponding to their respective isoelectric point. This allows one to separate the compounds according to their isoelectric point and to extract the migrating compounds from the chemical buffering system, and to recover the purified compounds in solution, preferably at various pI, so that they are not lost.

In contrast to the aforementioned Off-Gel electrophoresis technique, it has been found here that the performance of the separation could be improved by a special disposition of the electrical means. Indeed, in the present invention, the electrical field is not necessarily produced along the chemical buffering system only. In contrast, by applying the electrical field in the two extreme compartments containing the analyte solution (or even in all compartments of the apparatus), both the analyte solutions and the chemical buffering system are polarized, the strength of the electric field depending on the resistance (and conductivity) in each compartment and each portion of the contacting chemical buffering system. The charged compounds will then migrate along the lines of current, and due to the specific geometry of the apparatus and the position of the electrodes, the electric field is maximal in the direct fluidic connections (i.e. at the intersection(s) between two adjacent compartments). As the charged compounds follow the lines of current, they will be forced towards these intersections and will preferentially migrate through the direct fluidic connections. In addition, by approaching the direct fluidic connections, the migrating compounds reach a locus which is buffered at a pH imposed by the chemical buffering system. If a migrating compound has a pI corresponding to that pH value, it will be neutralized by the chemical buffering system and mainly diffuse back in the solution, (without penetrating into the chemical buffering system when this chemical buffering system is immobilized like e.g. in a gel). This phenomenon is increased by the placement of the electrodes inside the compartments, because the electrical field is more important in the analyte solution than in the chemical buffering system. In this manner, the separation rate is larger than in the previously disclosed Off-Gel technology, and the recovery is greatly improved.

In some cases, a thin layer fluidic connection (or direct fluidic connection), buffered by the chemical buffering system, is placed between the compartments in order to enhance the recovery of the proteins or other analytes after the separation. The thin layer fluid connection may be integrated within the chemical buffering system, for example it may be located in a channel formed in the chemical buffering system. Alternatively, the thin layer fluid connection may be located in a part of the apparatus separating the compartments. The terms "thin layer fluidic connection" or "direct fluidic connection" as used herein thus refer to one or a plurality of openings between two adjacent compartments. The opening is filled with a solution and has one dimension, width or diameter, which is small enough to prevent substantial natural convection but allows diffusion and migration of molecules between two adjacent compartments. This direct fluidic connection is generally placed in at least one portion of the wall separating the compartments, this wall being a solution resistant material. In a preferred embodiment, the thin layer fluidic connection is a hole or a micro-channel or an array of holes or micro-channels or a hollow passage that is directly formed in the walls separating two adjacent compartments and/or that is supported in a membrane, a fritted glass, a filter or the like, such pierced membrane, fritted glass, filter or the like being placed in the walls separating two adjacent compartments. In some applications, it may indeed be advantageous that each wall separating two adjacent compartments directly comprises an immobilized chemical buffering system that integrates such direct fluidic connection. When the thin layer fluidic connection is a hole, a micro-channel, an array of holes or micro-channels or a hollow passage, it may be advantageous to insert a solid support (such as a membrane, a fritted glas, a filter of the like) in such hole, micro-channel, array of holes or micro-channels or hollow passage in order to minimize convection and hence prevent physical movement and hence mixing of the solution between two adjacent compartments.

The separation method can be arranged to fit with various formats, means and apparatus that are generally used in life sciences. Separation and purification may thus for example be performed in conventional micro-titer-plates. The method does not require hydraulic flow. The neutral compounds of interest can be directly recovered in solution after purification and be analyzed by various analytical techniques such as mass spectrometry (MS), immunoassay or other type of biochemical analysis.

Separation and purification are performed in a (multi)compartment set-up. The (multi)compartment set-up is composed of at least two adjacent compartments without limitation in number, shape, dimension or volume. Depending on the geometry of the device, the chemical buffering system may or may not be considered as a wall closing the (multi)compartment set-up. Moreover, depending on the geometry of the (multi)compartment set-up, the chemical buffering system may be inserted in different positions. In some cases, all the compartments are independent, i.e. without direct fluidic connections. However, in some cases a thin layer fluid connection is placed between the compartments, In both cases, the compartments are always interconnected by mean of the chemical buffering system since they all contain a defined part of this system.

The immobilized chemical buffering system serves to fix the pH in the portion of this chemical buffering system which is in contact with the analyte solution. At least one portion of the chemical buffering system contacting the compartments may have a defined pH value or a defined pH gradient. The chemical buffering system is thus capable of separating the compounds by isoelectric point at a fixed pH or in a pH gradient. Different degrees of purification can be obtained depending on the pH range which is distributed over the (multi)compartment set-up and on the number of compartments. Several chemical buffering systems exhibiting similar or different pH ranges can be used simultaneously in different (multi)compartment set-ups to perform the parallel purification of one or several complex samples such as cellular extracts.

The term "chemical buffering system" (or "chemical buffering means") as used herein thus refers to any system by which the separation of charged compounds from globally neutral compounds can be performed due to the pH value or the pH range that it imposes on the analyte solution. In the present invention, the chemical buffering system is a buffer added to, the analyte solution (like e.g. an ampholyte) or it consists of buffering molecules immobilized on a support, that may be immobilized by covalent binding. It can be, but is not limited to, an immobiline gel or can be a fluid solidified in a support selected from either a polymer matrix, a fritted glass, a porous membrane, a filter or any combination thereof. In some applications, the immobilized chemical buffering system may be modified in order to avoid adsorption. It may be disposable.

A special disposition of electrical means is used. The electrical means may be integrated within the chemical buffering means. The electrical means may comprise electrodes and in some embodiments, an electrode is inserted in each compartment. In other cases, only two electrodes are used and are then respectively inserted in two compartments placed at each extremity of the set-up. When a potential difference is applied between the analyte solution and the chemical buffering system, it is possible to discriminate between charged compounds and compounds that are globally neutral at a given pH.

In each compartment, an electric field is present which forces the analyte to cross the gel or the thin layer fluid depending on its local charge. A potential difference is applied between different compartments in order to provide a voltage between each compartment and the solution and not only within the chemical buffering means itself. There are no restrictions on the material, size, geometry and position of the electrodes. In one embodiment, the electrodes comprise wires introduced into the top of the compartments whereas in another embodiment the electrodes comprise disks placed at the bottom of the compartments. The electrodes may be macro- or micro-electrodes.

The electrodes may be operated by an external power supply. Any voltage value and voltage form that the (multi) compartment set-up can tolerate may be used. A cooling device may be necessary to dissipate the generated heat.

In one embodiment, the electrodes are bare, whereas in another embodiment they are provided with means for protecting them from adsorption, contamination or redox reaction (notably with compounds present in the analyte solution), such as a membrane or a polymeric material.

When there is no direct fluidic connection between the compartments, the neutral compounds (pI=pH) in contact with the buffering system are maintained in the analyte solution, whereas the charged compounds (pI < or > pH) migrate into the chemical buffering system until they reach the point where the pH corresponds to their respective pI. Because of the special disposition of electric means and current lines, the charged compounds which migrate in the chemical buffering system are successively recovered in solution in the intermediate compartments before being extracted back in the matrix and before reaching the compartment where the pH corresponds to their pI and where they remain in solution. This configuration improves and ensures the recovery of the compound of interest in solution. This represents an improvement compared to the aforementioned OffGel device in which a potential difference was only applied through the chemical buffering system by means of two electrodes respectively placed at each extremity.

The situation is different when the compartments are interconnected with a thin layer fluidic connection. Indeed, in this case, the compounds do not migrate within the chemical buffering system but through the fluidic connection until they reach their own pI.

In a general manner, the compounds migrate towards the extremities of the set-up following the lines of current, which depend on the position of the electrodes, on the geometry of the whole set-up and on the nature of both the analyte solution and the chemical buffering system.

When a migrating compound reaches the point corresponding to its respective isoelectric point (pH=pI), it is recovered in solution in the corresponding compartment. It is thus possible to separate one or several compounds of interest from a mixture containing several compounds.

The invention allows the rapid elimination of undesired ions including salts, charged species or bases, buffer components or ampholytes from a solution. The chemical buffering system is there only to serve as a pH filter between both compartments, similarly to the role of the membrane in Righetti (supra). On the other hand, this system avoids the use of two membranes per compartment, one having a higher and the other a lower pH than the desired pH.

The neutral compounds of interest can be directly recovered in solution in the compartments after purification. The advantage is that no extraction with chemicals is necessary which simplifies the procedure and reduces the effect of chemicals on the compounds of interest.

However, the invention can also be used to accumulate the compounds of interest in the chemical buffering system and be considered as a preconcentration technique when the solution is distributed to each hole. This is a fundamental difference from OffGel electrophoresis, where the proteins which enter the gel can not be extracted again in other compartments unless their pI is at the extremity of the immobilized pH gradient in contact with the cathodic and the anodic compartment.

The method of the invention may be semi- or totally automated. In particular, the apparatus may comprise an automated device allowing both the filling and the emptying of the compartments as well as the sequential displacement of the (multi)compartment set-up in x, y and/or z direction. The system may alternatively be connected with a simple micropipette for mechanical pumping and manual displacement of the (multi)compartment set-up.

Agitation could be induced in the (multi)compartment set-up in order to increase the convection. Moreover, agitation could be useful to avoid the formation of concentration gradients and to insure the homogeneity of the analyte solution.

For protein purification, it could be useful to control the temperature of the device and to add means avoiding precipitation. In addition, for some applications, it may be advantageous to add buffers or ampholytes to the analyte solution, notably in order to facilitate the focusing of the compounds that have reached their pI.

The "analyte" is any biological or chemical compound which is neutral at the pH or in the pH interval defined by the chemical buffering system in contact with the analyte solution. In a preferred embodiment, the analyte is an ionizable biological compound such as one or more proteins, an enzyme, a peptide or a compound containing a peptide or a protein moiety such as a glycoprotein. It can also be a nucleic acid, complex lipid or complex carbohydrate. It may also be various isoforms of a protein, antigens or antibodies such as monoclonal antibodies.

A charged compound, namely any compound that is charged at the pH or in the pH interval defined by the chemical buffering system in contact with the analyte solution, may be present. The charged compound is preferably an acid, a base, an ampholyte or a permanently charged compound like for example a dissociated salt. The charged compound is extracted from the compartments into the chemical buffering system upon electrophoretic separation according to the present invention. It can be still further extracted out of the chemical buffering system into a solution and may be the compound of interest, i.e. the analyte.

The term (multi)compartment set-up refers to a commercially available or home-made device composed of one or several compartments without any restriction of number, shape, dimensions or volumes, which can be varied as required by the specific application. The (multi)compartment setup may be for example conventional micro-titer-plates. All the compartments are in a series.

The (multi)compartment set-up may be fabricated from any suitable material. Thus, it may be fabricated from solid plastics such as e.g. Plexiglas®. It may also be molded out of a thermoplastic resin or made by any other suitable manufacturing processes. The material should have chemical resistance for example to the analyte solution, the electric current, weak acids or bases and oxidants. For some applications, it may be useful to have some degree of transparency. The apparatus may be modified in order to avoid adsorption of compounds on its walls.

Depending on the geometry of the (multi)compartment set-up, the chemical buffering system may be inserted in different positions. In one embodiment, the chemical buffering system is placed at the bottom of a (multi)compartment device. This can for example be fabricated from wells similar to conventional micro-titer plates with holes pierced in the bottom wall of each well. The (multi)compartment set-up can then be placed on top of the chemical buffering system. In another embodiment, the chemical buffering system may be placed in a vertical position. In this case, holes are pierced in the vertical wall of each compartment and the chemical buffering system is then introduced through these holes.

This invention allows the rapid elimination of undesired ions including salts, charged species, acids or bases, buffer components or ampholytes from a solution. In this case, the compounds of interest are recovered in solution and the chemical buffering system can be regarded as a waste reservoir.

In another embodiment, the invention may be used to accumulate charged compounds that are of interest in the chemical buffering system.

In some embodiments of the invention, the "dead" area between the compartments is minimized, by making the compartments contiguous where they contact the chemical buffering means, so that only a very small portion of the chemical buffering means is not directly in contact with the sample solution. Such a geometry allows the number of molecules that penetrate into the chemical buffering system to be minimized. In this manner, the number of molecules that remain entrapped within the chemical buffering system at the end of the purification is minimized. Indeed, as the chemical buffering system is the only available passage for the current between two compartments, there is a very large density of current at the intersection between the chemical buffering system and two adjacent compartments. Due to the positioning of electrodes in each of the compartments, charged species migrating through this small portion of the chemical buffering system are directed towards the electrodes and hence towards the solution bulk of each reservoir. Only the molecules that are globally neutral in this small portion of the chemical buffering system will remain in it after the separation.

In another embodiment, a protective layer is added in the device of the invention in order to minimize the portion of the chemical buffering system contacting the sample solution. In this manner, adsorption of the molecules onto the chemical buffering system is minimized.

BRIEF DESCRIPTION OF THE DRAWINGS

The invention will now be described in more detail, by way of example only, with reference to the accompanying drawings, in which.

DETAILED DESCRIPTION OF THE PREFERRED EMBODIMENTS

Figure 1:
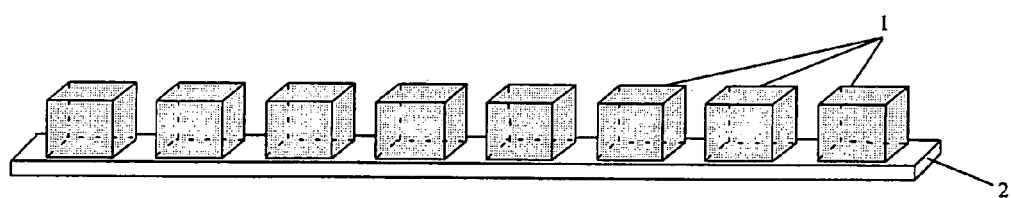
FIGS. 1A and 1B schematically show apparatus according to first and second embodiments of the invention respectively, but not showing the electrodes.
Figure 1:
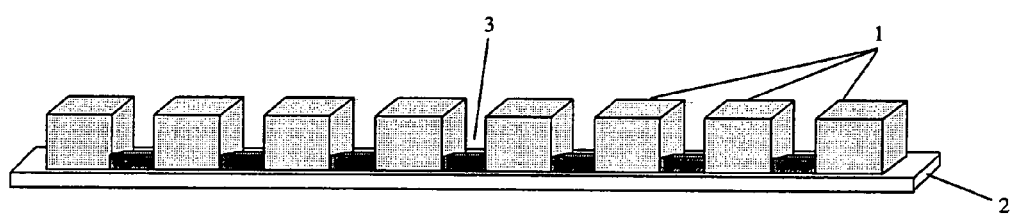

FIGS. 1A and 1B show how the multi-compartment set-up and the chemical buffering system of the invention can be positioned. A multi-compartment set-up, which is an array composed of eight compartments 1 is presented as an example. The multi-compartment setup is placed on top of the chemical buffering system 2. In this case, the compartments are open at their top and bottom extremities. All the compartments are interconnected by mean of the chemical buffering system. In FIG. 1A, there is no direct fluidic connection between the compartments. In FIG. 1B, a thin layer fluidic connection 3 is placed between the compartments 1, in a part of the apparatus defining the compartments. The solution trapped inside the thin layer fluidic connection can be buffered by diffusion of H+ or OH− ions from the chemical buffering system. It also enables the analyte solution to migrate through depending on its charge at this given pH. Natural convection of solution is avoided.

Figure 2:
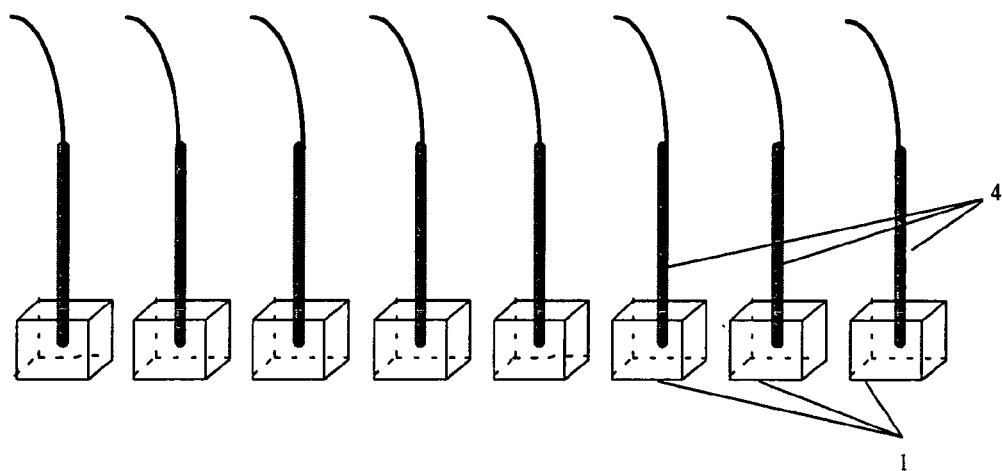
FIGS. 2A, 2B and 2C schematically show alternative arrangements of electrodes.
Figure 2:
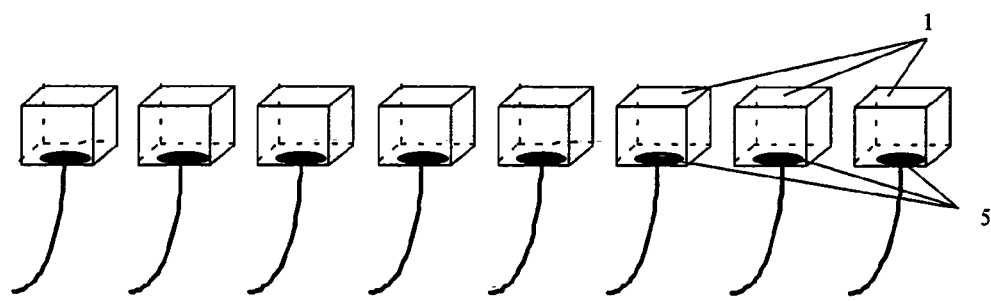
Figure 2:
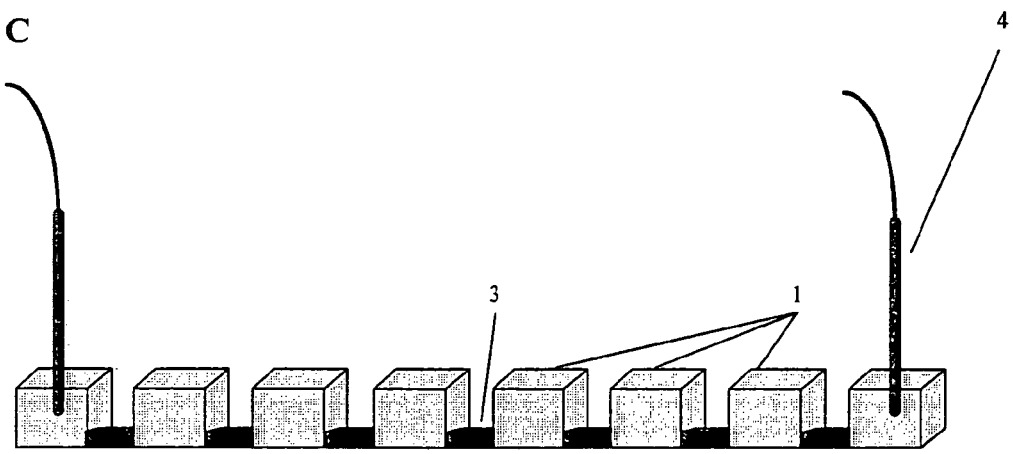

FIGS. 2A, 2B and 2C show how electrodes can be placed in the multi-compartment set-up. In all cases, the chemical buffering system can be placed at bottom or vertically in the multi-compartment set-up. In FIG. 2A, the electrodes comprise wires 4 which are introduced vertically, one in the top extremity of each compartment 1. In FIG. 2B, the electrodes comprise discs 5, one of which is positioned at the bottom of each compartment 1. In FIG. 2C, the electrodes comprise wires 4 which are placed in the top extremities of two of the compartments 1. In this case, only two electrodes 4 are used, each one being respectively placed in one of the compartments 1 positioned at the extremities of the set-up. A combination of the above-mentioned electrical means can be provided, depending on the application.

In the configuration of FIG. 2C, the pH in each compartment may be imposed directly by buffer molecules such as ampholytes that are added to the analyte solution and hence constitute the chemical buffering system. Upon application of the electric field, the compounds that are charged at the pH imposed by the buffers will migrate. In addition, in the case where a series of ampholytes is used to impose the pH in the various compartments, the ampholyte molecules will also migrate in the electric field, thereby creating a gradient of pH between the various compartments. In this manner, the ampholyte molecules will also impose a pH value or a pH gradient in each thin layer fluidic connection interconnecting the various compartments. As these thin layer fluidic connections allow to prevent convection and the mixing of the analyte solutions between two adjacent compartments, but the charged compounds will migrate until they reach a compartment in which the imposed pH encompasses their respective isoelectric point, thereby enabling efficient separation or purification.

Figure 3:
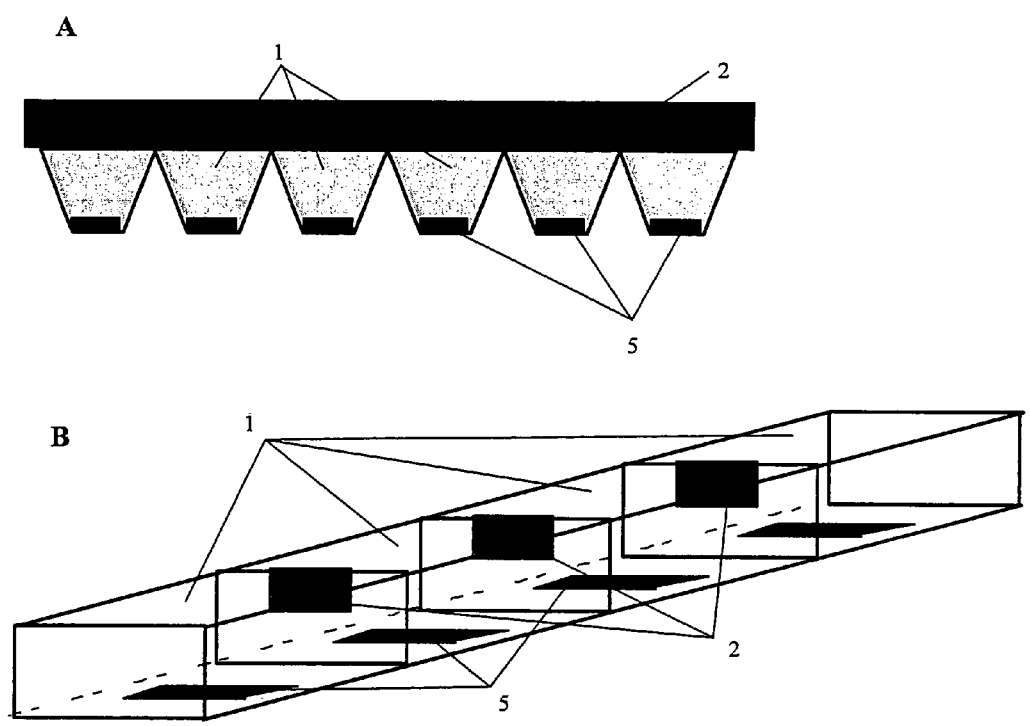
FIGS. 3A and 3B schematically show embodiments of apparatus according to the invention comprising contiguous compartments.

FIGS. 3A and 3B show example of devices according to the present invention where the "dead" area bordered by the chemical buffering system and two adjacent compartments is minimized. FIG. 3A shows an example of said device where the chemical buffering system is in contact with the edge of two adjacent compartments, whereas FIG. 3B shows an example where the chemical buffering system is made of a discrete series of chemical buffering systems directly placed in a portion of the wall contacting two adjacent compartments.

Figure 4:
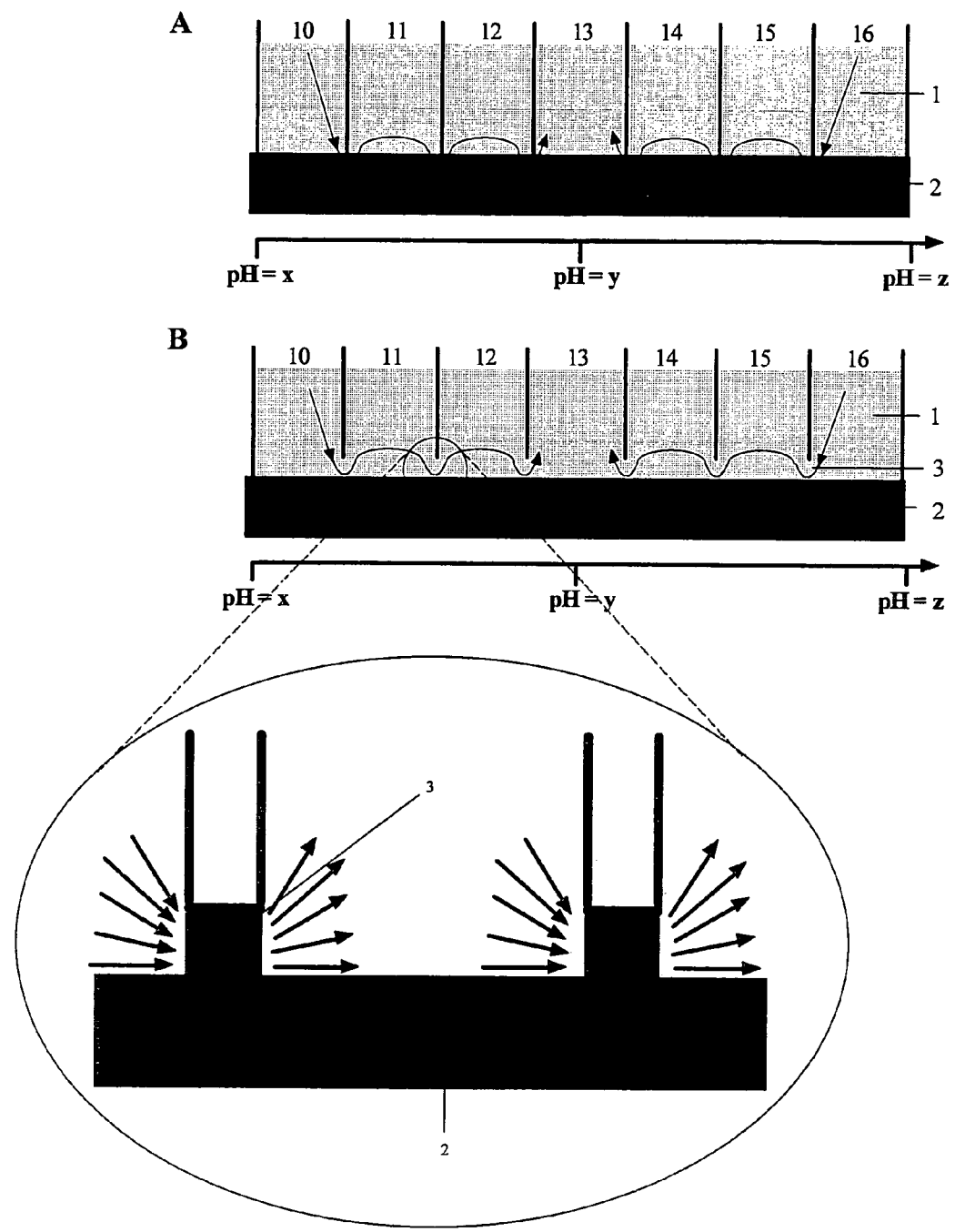
FIGS. 4A and 4B schematically show electrophoretic migration pathways in apparatuses according to two different embodiments of the invention.

FIGS. 4A and 4B each show the electrophoretic migration pathway of a molecule in an example of a multi-compartment set-up. A chemical buffering system 2 comprising an IPG gel with a pH gradient from x to z is placed under a multi-compartment set-up composed of 7 opened compartments 10 to 16. A molecule with a pI of y is caused to migrate by means of an electric field. An electrode is placed in each compartment (also referred to hereinafter as a well) and a potential difference is applied between each compartment. The electrodes are not shown for greater clarity.

In the case of FIG. 4A, there is no direct fluidic connection between the compartments and the molecule migrates within the chemical buffering system. When the molecule is present in the wells 10, 11 and/or 12 (pH <pI), it is positively charged and migrates towards the cathode until reaching the well 13 where it is neutral (pH=pI). On the other hand, when the molecule is present in the wells 14, 15 and/or 16 (pH>pI), it is negatively charged which induces its migration towards the anode. During migration, the molecule is recovered in solution in the successive intermediate wells before being extracted again in the matrix. The molecule migrates until it reaches the well 13 where the pH corresponds to its pI. This process ensures the recovery of the compounds of interest in solution. It is particularly useful when mixtures containing several compounds of interest will have to be separated.

In the case of FIG. 4B, the compartments 10 to 16 are interconnected by a thin layer fluidic connection 3. The major part of the analyte of interest does not migrate within the chemical buffering system but through the thin layer fluidic connection where the electric field is maximal. The molecule migrates until it reaches the well 13 where the pH corresponds to its pI.

Figure 5:
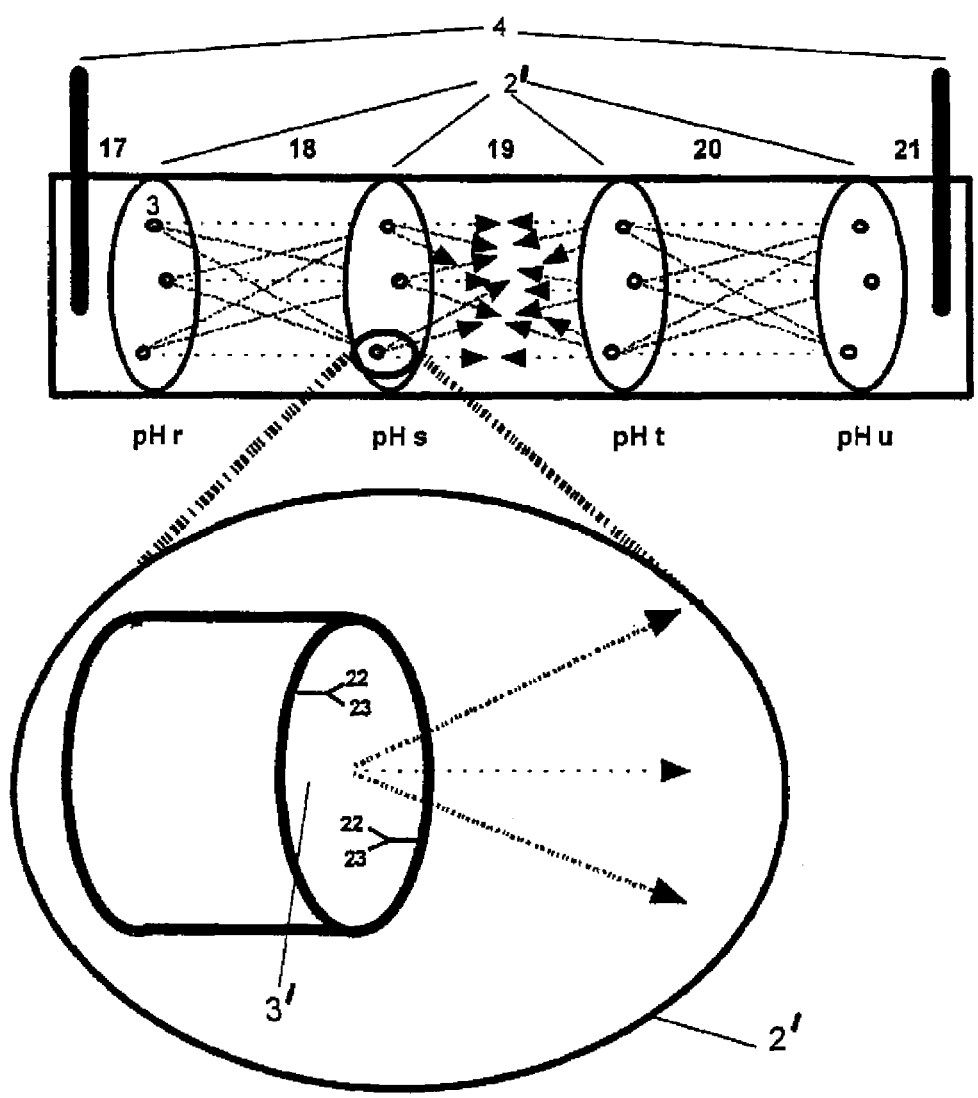
FIG. 5 schematically shows an embodiment of apparatus according to the invention in which the chemical buffering means is supported by membranes.

FIG. 5 shows the electrophoretic migration pathway of a molecule in another type of multi-compartment set-up of the present invention. Four chemical buffering means 2' which exhibit different fixed pH values respectively equal to r, s, t and u are used. They are each placed vertically in a holder where they delimit five closed compartments 17 to 21. Two wire electrodes 4 are respectively placed in the end compartments 17 and 21. The chemical buffering means 2' are supported on membranes having microholes allowing the passage of charged compounds from one compartment to the next and thus forming. thin layer fluid connections 3'. At the same time, the physical mixing of the solutions present in the different compartments 17 to 21 is avoided. The diameter of the microholes is preferably less than 2 mm. The microholes bear the same buffering molecules as are present in the chemical buffering means. The buffering molecules can be, but are not limited to, immobilines with immobilized chemical groups such as COOH 22 and $NH_3^+$ 23. The pH in the holes is equivalent to the global pH exhibited by the chemical buffering means 2'.

A molecule with a pI comprised between pH s and pH t (compartment 19) is caused to migrate by application of an electric field between the two electrodes 4. A pH gradient ranging from r to s is then established between the compartments. The current lines and the migration pathway of the molecule are schematically represented by dashed arrow lines in FIG. 5. When the molecule is present in compartment 17 and/or 18 (pH<pI), it is positively charged and migrates towards the cathode until it reaches compartment 19 where it is neutral (pH=pI). On the other hand, when the molecule is present in compartment 20 and/or 21, it is negatively charged which induces its migration towards the anode. Using this configuration, the molecules migrate preferentially through the microholes, where the electric field is maximal, and not directly through the chemical buffering means 2'. This avoids precipitation problems that can occur when the molecules migrate directly through the chemical buffering means. The molecule migrates until it reaches compartment 19 where the pH corresponds to its pI and where it can be recovered in solution.

EXAMPLE I

Methylene blue was obtained from Fluka. Immobiline DryPlates (pH range 4.0 7.0, 11 cm), which are immobilized pH gradient. (IPG) gels, were from Amersham Pharmacia Biotech. All the experiments were performed in MilliQ water.

The multi-compartment set-up was a micro-titerplate (Millipore) composed of 96 (12×8) plastic wells (id 6 mm) opened at top and bottom extremities. In this experiment, the chemical buffering means comprises IPG gels that are cut to strips with a width of 7-8 mm, which is necessary to avoid solvent leakage. The length of the gel depended on the pH gradient to be distributed between the different wells. Reswelling of the gels was carried out for 1 hour at room temperature in water. The wells of the micro-titerplate were placed on top of the reswelled gel.

The wells were filled with 75 µl of analyte solution or water. A platinum electrode 4 was placed in the top extremity of each well. The electrodes were operated with a Landis & Gyr power supply. Some resistances were placed between the electrodes in order to apply the same voltage between each well.

Digital photographs were taken with a numerical camera (Camedia C-2020 Z Olympus) and were treated with Olympus Camedia software.

The experiment was performed using three adjacent wells placed on top of an IPG gel, respectively on the pH 4.1, 4.4 and 4.6 lines. 75 µl of a 1 mM methylene blue solution were placed in the left hand side well (anodic) at pH 4.1. The central and the right side wells (pH 4.4 and 4.6, respectively) were filled with water.

In these conditions, methylene blue was charged over the whole pH range imposed by the gel since it is a permanent cation and it exhibited a blue color. The migration of this dye in the apparatus towards the cathodic well was thus easily followed upon application of a constant electrical potential (100 V between each well). Methylene blue did not migrate directly towards the cathodic well, and digital photographs taken after 10 minutes demonstrated that methylene blue was previously recovered in solution in the central well. After one hour, the migration was almost complete since methylene blue was recovered in solution in the right hand side well.

These results demonstrate the efficiency of the present invention for the electrophoretic migration of an analyte and its recovery in solution. The results clearly demonstrated that the analyte was recovered in solution in the intermediate compartment before reaching the final compartment. This comes from the distribution of the current lines due to the presence of one electrode in each well. This process can be generalized to any number of intermediate compartments.

Figure 6:
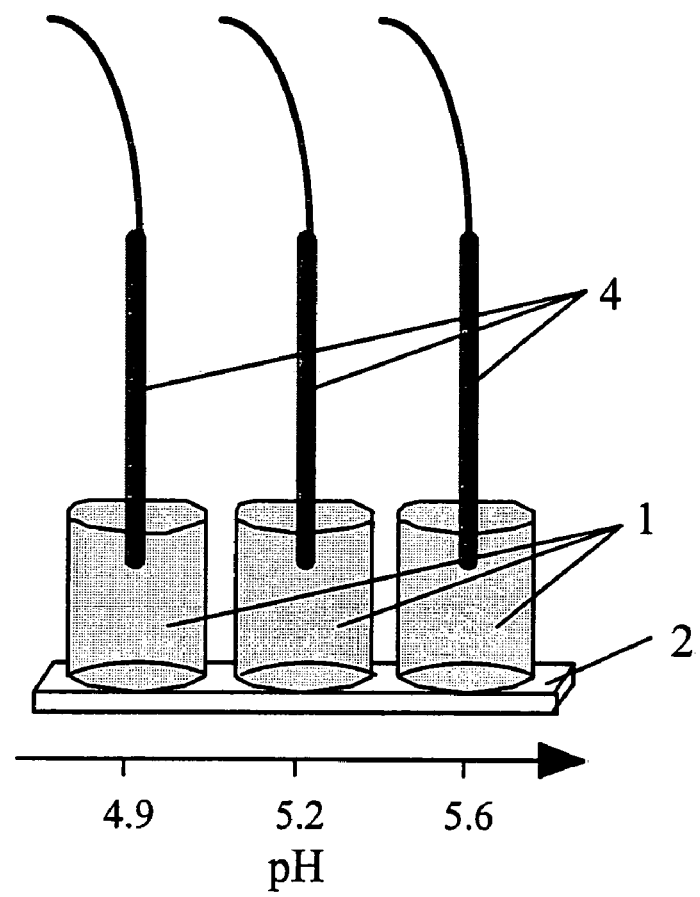
FIG. 6 schematically shows an experimental set-up used for the separation of β-lactoglobulin B and myoglobin.

EXAMPLE II

β-lactoglobin B and equine myoglobin were purchased from Sigma. An aqueous solution of 500 µM β-lactoglobin B (pI=5.2) and 500 µM equine myoglobin (pI=7.0) was prepared. In this case, the experiment was performed using three adjacent wells placed on top of an immobiline gel, respectively on the pH 4.9, 5.2 and 5.6 lines. The other elements of the experimental set-up (multi-compartments, electrodes, chemical buffering system and power supply) were the same as in Example I above. The protein solution was placed in each of the three wells, which also contained an electrode. The experimental set-up used for this experiment is shown in FIG. 6.

MS assays were performed with an Ion Trap LCQ duo mass spectrometer (Finnigan) in a medium composed of 50/49/1 (v/v/v) $CH_3OH/H_2O/CH_3COOH$. The experiments were performed at a flow-rate of 5 µl/min under a polarization of 5 kV.

Figure 7:
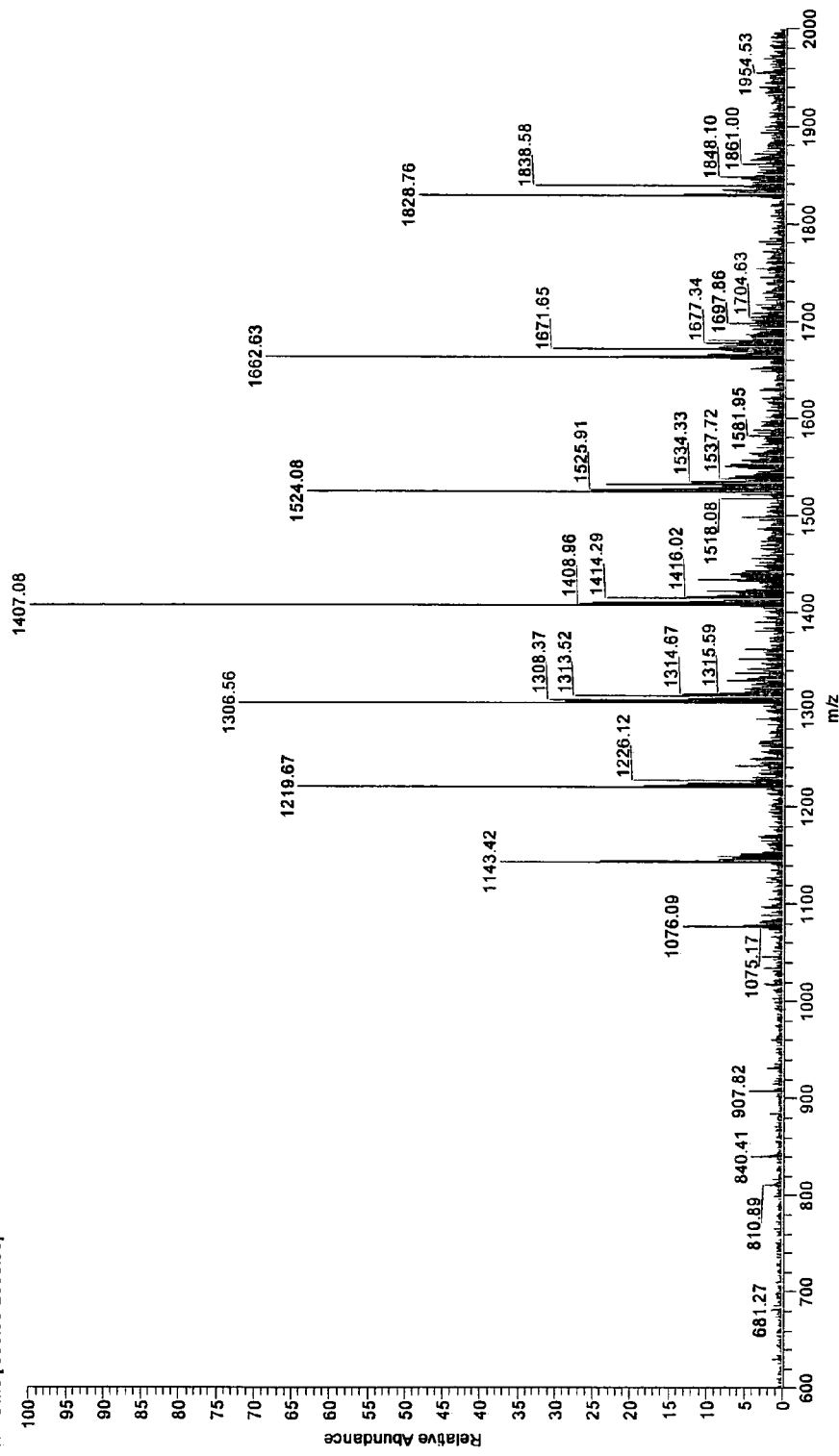
FIG. 7 is a mass spectrum of β-lactoglobulin B alone (500 μM)
Figure 8:
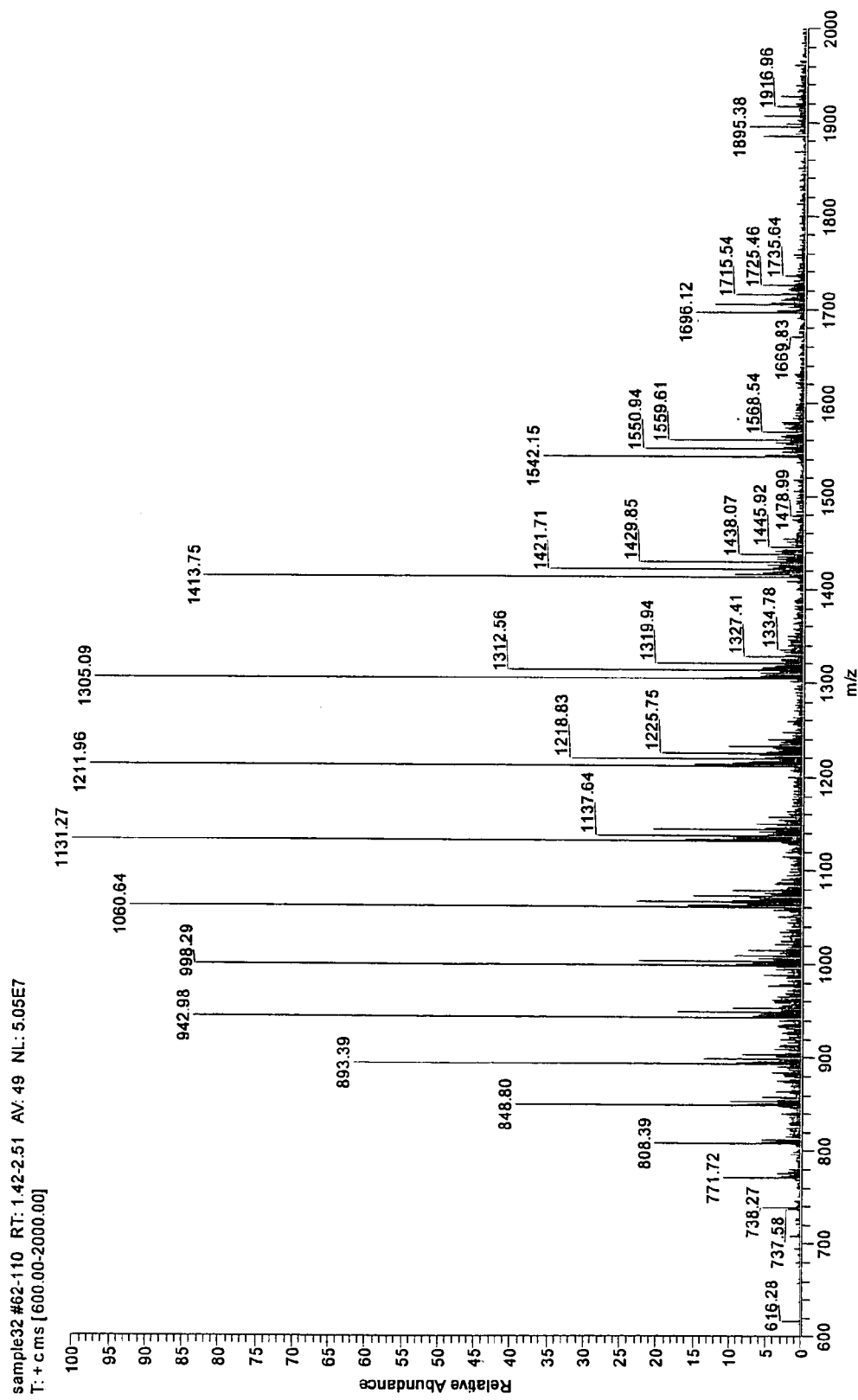
FIG. 8 is a mass spectrum of myoglobin alone (500 μM).
Figure 9:
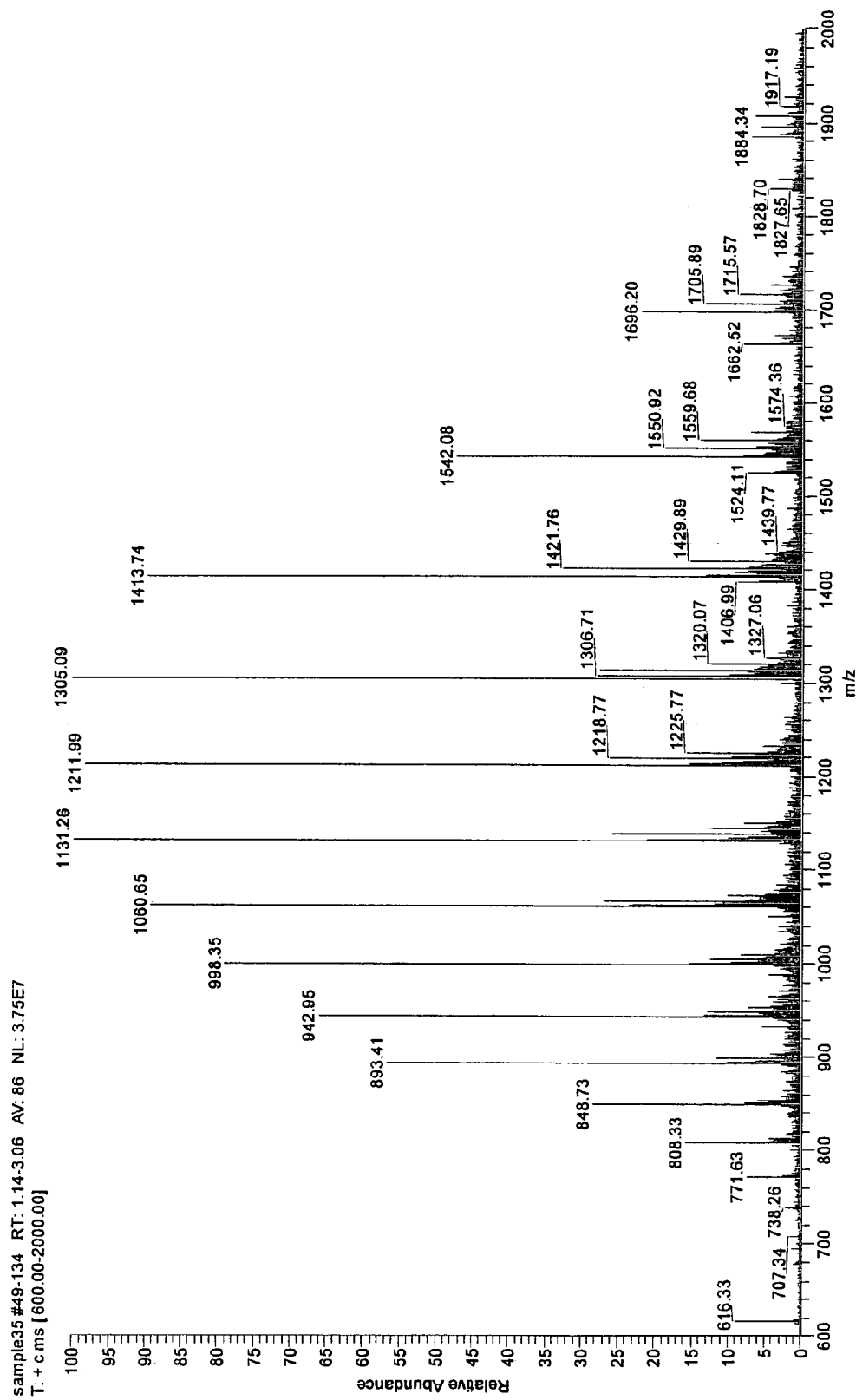
FIG. 9 is a mass spectrum of a protein mixture containing 500 μM β-lactoglobulin B and 500 μM myoglobin before electrophoretic separation.

The individual mass spectra of β-lactoglobin B and myoglobin are respectively presented in FIGS. 7 and 8. The mass spectrum of the protein mixture placed in each well is presented in FIG. 9. In this case, peaks that are typical of both proteins are observed. However, a predominance of myoglobin is observed. This comes from the fact that myoglobin ionization is easier than that of β-lactoglobin B.

A potential of 100 V was applied for 90 minutes between the three wells. Mass spectrometry experiments were then performed with the solutions contained in each well. The mass spectrum obtained from the left hand side, the central and the right hand side wells in FIG. 6 after 90 minutes of migration are respectively presented in FIGS. 10, 11 and 12.

Figure 10:
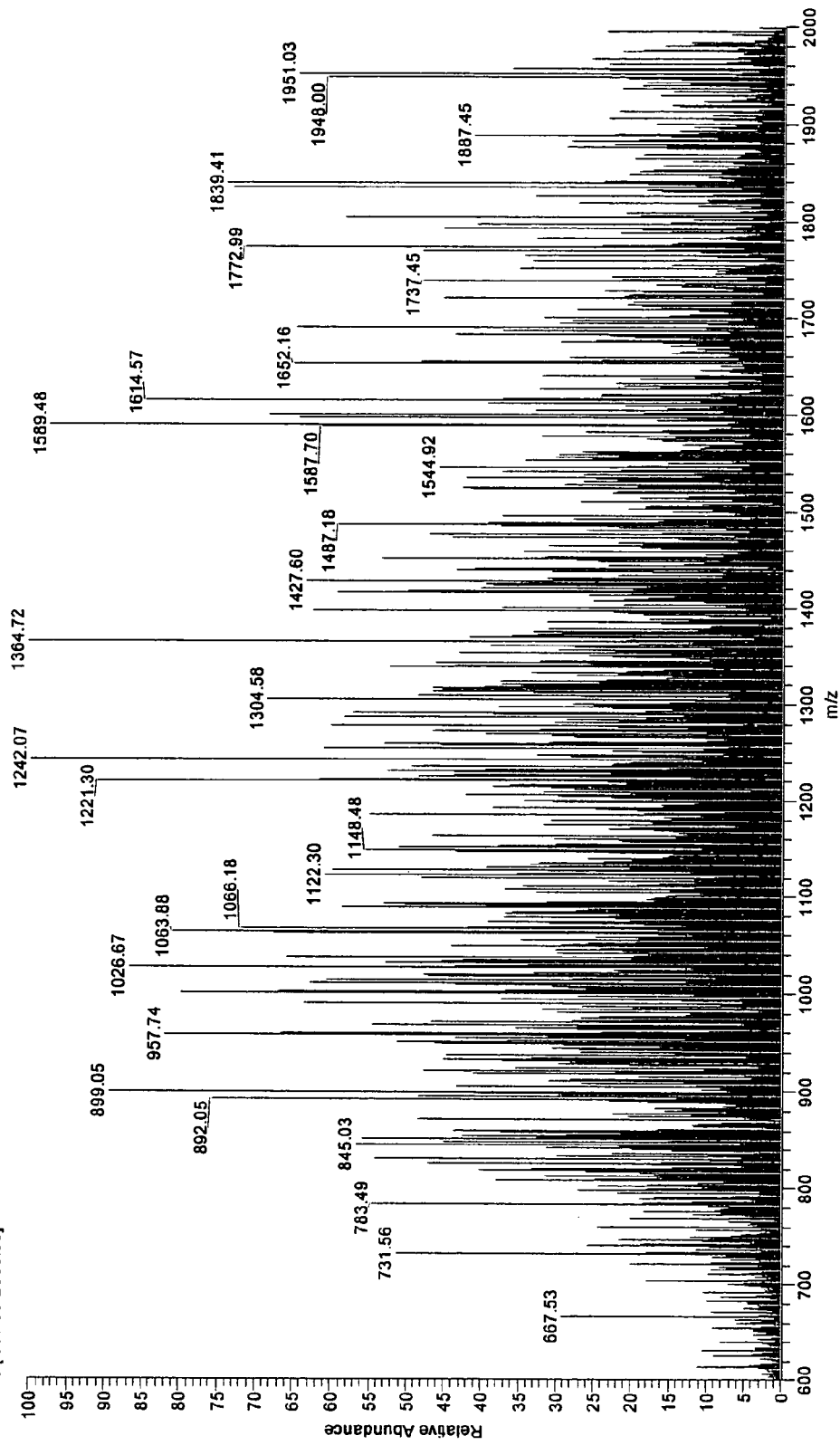
FIG. 10 is a mass spectrum obtained from the left hand side compartment in FIG. 6 (pH=4.9) after 90 minutes of migration of the mixture of FIG. 9.
Figure 11:
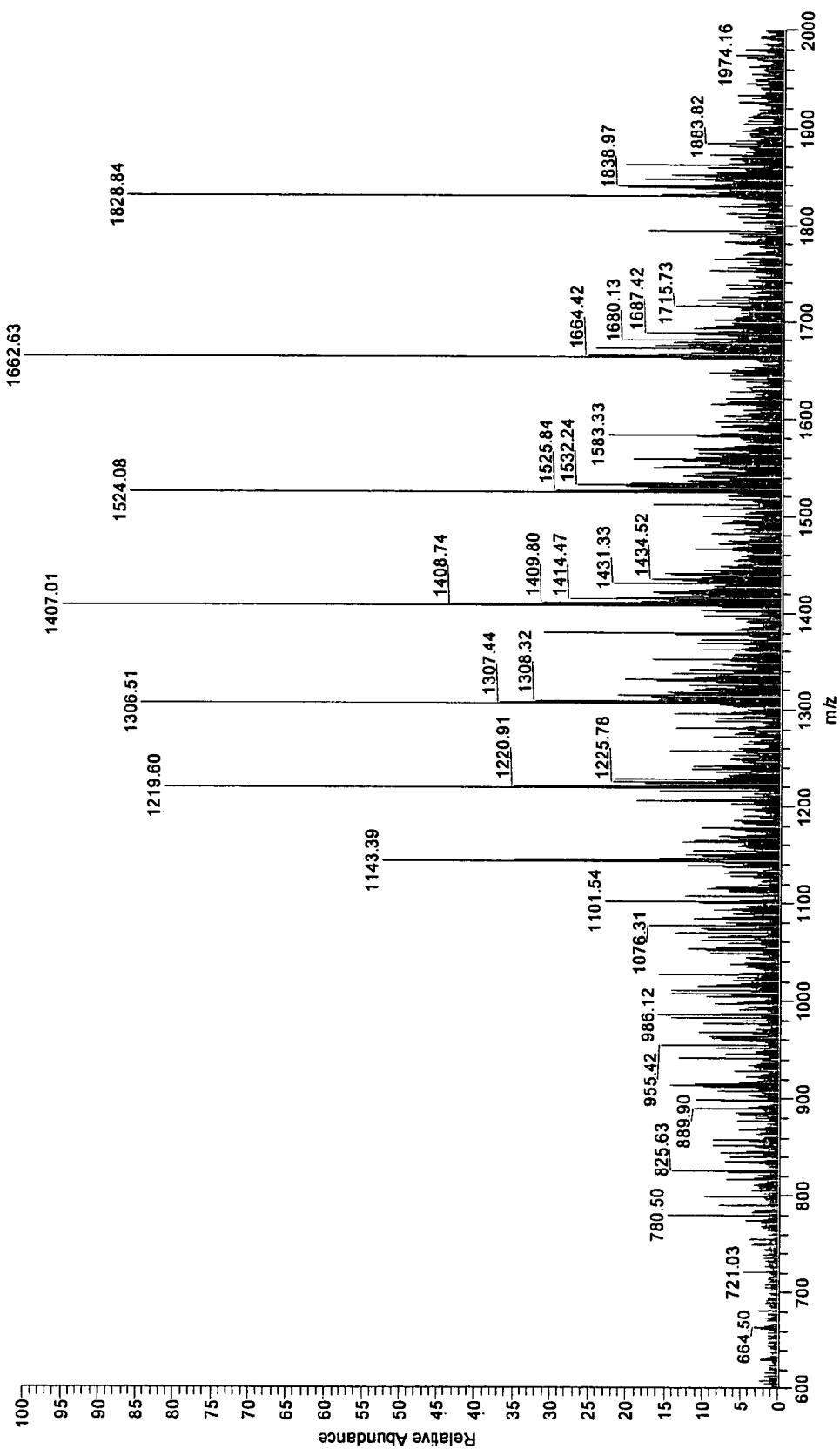
FIG. 11 is a mass spectrum obtained from the central compartment in FIG. 6 (pH=5.2) after 90 minutes of migration of the mixture of FIG. 9.
Figure 12:
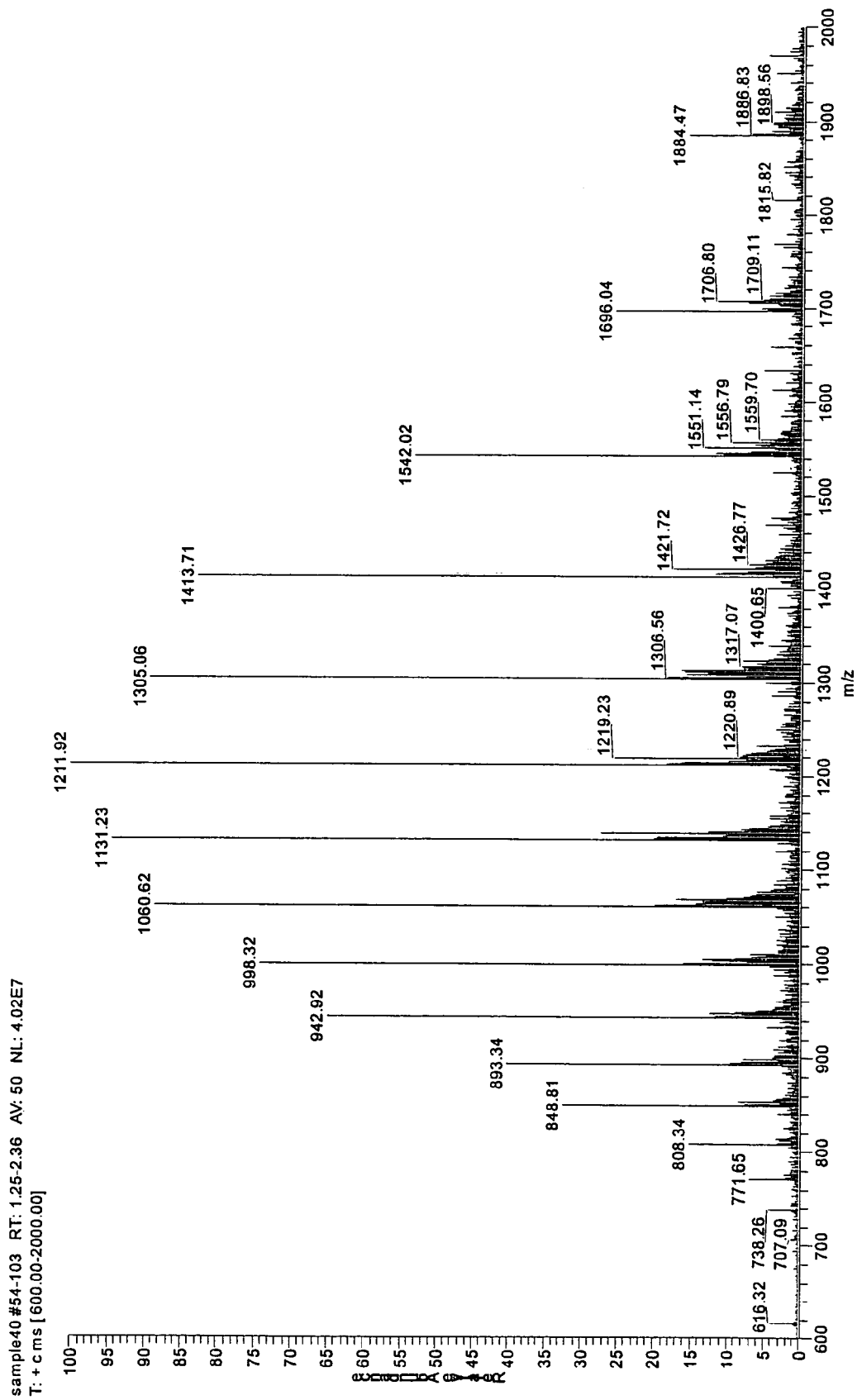
FIG. 12 is a mass spectrum obtained from the right hand side compartment in FIG. 6 (pH=5.6) after 90 minutes of migration of the mixture of FIG. 9.

As can be seen in FIG. 10, after 90 minutes of migration, the left hand side well (pH=4.9) no longer contained any proteins. After 90 minutes, the central well (pH=5.2) contained predominantly β-lactoglobulin B and residual traces of myoglobin (FIG. 11). On the other hand, the right hand side well (pH=5.6) contained predominantly myoglobin and residual traces of β-lactoglobin B (FIG. 12).

These results conform to what was expected. Indeed, since the pI of myoglobin is 7.0, it was charged over the whole pH range imposed by the gel and migrated towards the right side well (pH 5.6) where it was recovered in solution at the end of the experiment. The pI of β-lactoglobin B is 5.2. In the acidic gel extremity near the anode, this protein was positively charged (pH in gel<pI) and migrated towards the cathode. On the other more basic gel extremity near the cathode, β-lactoglobin B was charged positively (pH in gel>pI) and it migrated towards the anode. The migration of β-lactoglobin B stopped in the central well where the protein was neutral (pH in gel=pI) and where it was recovered in solution at the end of the experiment.

These results clearly demonstrate the purification principle based on isoelectric separation according to the present invention. This invention can be used for the efficient purification of a protein mixture. The purified proteins can be recovered very easily in solution and used directly for further analyses such as MS.

EXAMPLE III

Figure 13:
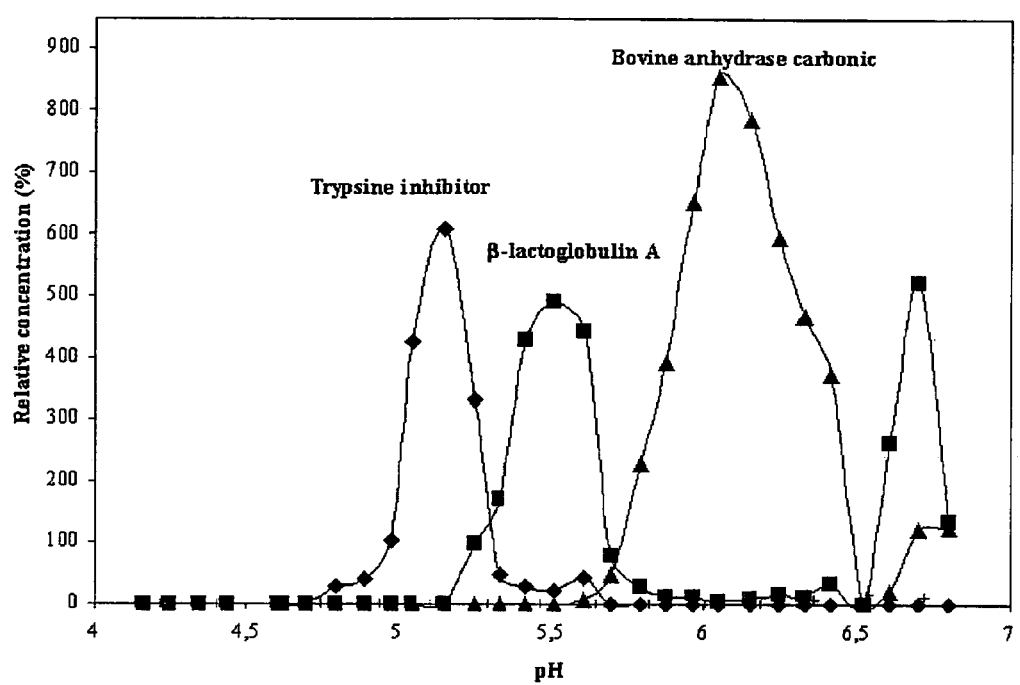
FIG. 13 shows the distribution and the concentrations of three proteins after electrophoretic separation in a multi-compartment apparatus according to the invention.
Figure 14:
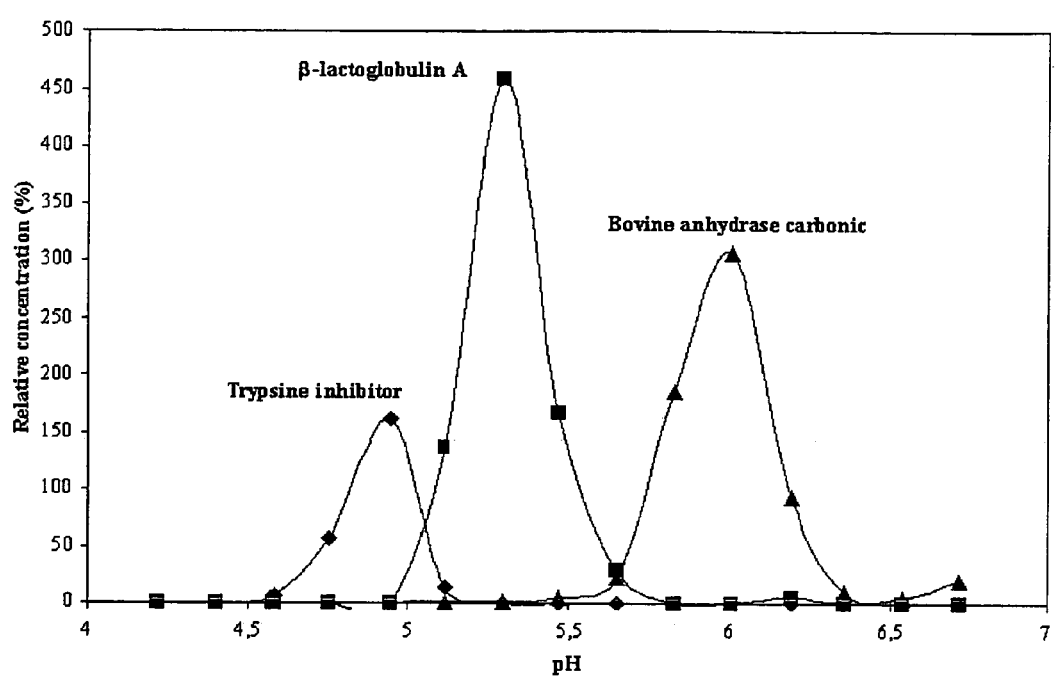
FIG. 14 shows the distribution and the concentrations of three proteins after electrophoretic separation in an alternative multi-compartment apparatus.

In order to demonstrate the unique feature of direct fluidic connection between the compartments, a comparison experiment between two multi-compartment IEF separations has been conducted whereby in one experiment, a direct fluidic connection is present (FIG. 13) and in the other, no direct fluidic connection is present (FIG. 14). The experiments have been conducted by means of 21 cm long polyurethane devices composed of 30 compartments. The direct fluidic connections were obtained by opening holes at the bottom of the walls separating the compartments. Control experiments were performed using the same prototype but without fluidic connections. The geometries of the non modified and modified devices are similar to the set-up respectively presented in FIGS. 4A and 4B. The polyurethane multi-compartment devices are compatible with the strip holders and with the IPGphor power supply from Amersham Biosciences which were used to perform electrophoretic separations.

Immobiline pH gradient (IPG) strips of length 24 cm with a linear pH gradient ranging from 4.0 to 7.0 (Amersham Biosciences) were placed under the devices after 15 minutes reswelling in water at room temperature. The strips associated with the polyurethane devices were then placed in cup loading strip holders and connected with the IPGphor power supply. Trypsin inhibitor (pI 4.6), β-lactoglobin A (pI 5.2) and bovine anhydrase carbonic (pI 5.9) were obtained from Sigma. A protein solution containing 250 μ/ml of each protein was prepared in 10% sucrose containing 0.1% IPG buffer pH 4.0-7.0 (ampholytes) (Amersham Biosciences). 100 μl of the protein solution were dispensed in each compartment. An electrode cup was placed at each extremity of the gels, the anode and the cathode being respectively placed on the sides of lowest and highest pHs. A wetted piece of filter paper was placed between the gel and the electrode.

The protein content in each compartment after electrophoresis as well as the starting protein solution were analyzed with protein chips and the Bioanalyzer from Agilent Technologies. The relative concentrations were calculated by reporting the concentrations in a given well after fractionation to the initial concentration in the starting solution.

In the case of trypsin inhibitor and bovine anhydrase carbonic, the recovered concentrations were higher with the apparatus comprising direct fluidic connections between the compartments (FIG. 13) than with the apparatus having no direct fluidic connection (FIG. 14). Concerning β-lactoglobin A, the recovered concentrations were in the same range with both apparatuses.

The high concentrations recovered with the apparatus comprising direct fluidic connections result from the fact that with this configuration, the major part of the proteins does not migrate within the chemical buffering system but directly through these thin layer fluidic connections where the electric field is maximal. This prevents the proteins from precipitating in the gel and explains the improvement of the recovery yields of the proteins.

In addition, it is worth mentioning here that the chemical buffering system allows one to fix the desired pHs or pH ranges of the contacting solution in the various compartments, which is necessary to perform the separation. However, the direct fluidic connections create a sort of preferential path for the migrating molecules, which molecules it is pass more easily directly from one compartment to the other along the thin layer fluidic connections (and hence in solution) than by penetrating into the chemical buffering system before being extracted again in the adjacent compartment (and so on until the migrating species reaches its pI). The direct fluidic connections therefore allows one to minimize the proportion of molecules migrating into the chemical buffering system itself, which was not possible to achieve in previously developed Off-Gel technology described in WO 01/86279 A1 and which favors the separation rate as well as the recovery of the separated molecules. All forms of the verb "to comprise" used in this specification have the meaning "to consist of or include".

The invention claimed is:

1. An apparatus for electrophoretic separation and purification of at least one charged and/or neutral analyte from a solution by isoelectric focusing, said apparatus comprising:
a series of at least two compartments having at least one wall portion composed of a chemical buffering means forming a non-convective liquid junction interconnecting said at least two compartments, and said chemical buffering means defining in each compartment of the series one of a fixed pH value or a pH gradient in its portion contacting said solution;
a thin layer fluidic connection between said at least two compartments allowing non-convective passage of solution from one compartment to another, said thin layer fluidic connection being one of a hole, a micro-channel, an array of holes or micro-channels, and a hollow passage; and said thin layer fluidic connection being characterised by a lower resistivity than that of said chemical buffering means, thereby providing a liquid junction interconnecting said at least two compartments having a higher conductivity than that provided by said chemical buffering means; and
electrodes placed in at least two of said compartments at extremities of the series for forcing said charged analyte and/or undesired charged compounds present in said solution to move from one of said compartments to another or to the other of said compartments by virtue of the charge of said analyte and/or said undesired charged compounds at the pH value or in the pH range defined by the portion of the chemical buffering means contacting said analyte solution in each individual compartment of the series.

2. An apparatus according to claim 1, wherein the chemical buffering means is selected from a group consisting of a gel comprising immobilized buffering molecules, ampholytes added to the analy and a fluid solidified on a support selected from a polymer matrix, a fritted glass, a porous membrane, a filter, and any combination thereof.

3. An apparatus according to claim 2, wherein said support contains micro-holes through which charged analyte and/or undesired charged compounds migrate upon application of an electric field.

4. An apparatus according to claim 2, wherein the chemical buffering means comprises covalently immobilized buffering molecules.

5. An apparatus according to claim 1, wherein portions of said chemical buffering means contacting each of said compartments have different resolving power, so that different degrees of purification are obtained in the compartments.

6. An apparatus according to claim 1, wherein said chemical buffering means contains a means for direct identification and/or quantification of a compound or a class of compounds that have been extracted from the analyte solution out of one of said compartments.

7. An apparatus according to claim 6, wherein said identification and/or quantification means is based at least on one of production of light, absorption of light, reaction with a blotting agent or label, generation of an electroactive species, specific molecular recognition of compounds, and recognition of a formation of an antigen-antibody complex or an enzymatic reaction.

8. An apparatus according to claim 1, wherein said chemical buffering means is disposable.

9. An apparatus according to claim 1, wherein said chemical buffering means comprises a waste reservoir.

10. An apparatus according to claim 1, wherein said thin layer fluidic connection is provided in at least one wall separating said compartments and/or in the chemical buffering means.

11. An apparatus according to claim 1, wherein said thin layer fluidic connection comprises means to prevent physical movement of the solution while allowing the passage of said charged analyte and/or said undesired charged compounds.

12. An apparatus according to claim 1, wherein said apparatus comprises one electrode in each compartment.

13. An apparatus according to claim 1, comprising means for protecting said electrodes from at least one of adsorption, contamination, and undesired redox reaction.

14. An apparatus according to claim 1, wherein at least one electrode is integrated within said chemical buffering means.

15. An apparatus according to claim 1, wherein said compartments are contiguous where they contact said chemical buffering means.

16. An apparatus according to claim 1, wherein said chemical buffering means is a continuous medium interconnecting all the compartments of the series.

17. An apparatus according to claim 1, wherein at least one of said compartments is connected to a hydraulic flow system to permit the analyte solution to flow through said at least one compartment.

18. An apparatus according to claim 1, wherein at least one of said compartments comprises coupling means permitting purified analyte to be passed from said at least one compartment into other separation and/or detection systems.

19. An apparatus according to claim 1, further comprising means for preventing precipitation of neutral analyte.

20. An apparatus according to claim 1, further comprising temperature control means.

21. An apparatus according to claim 1, further comprising means for inducing convection to homogenize the analyte solution.

22. An apparatus according to claim 1, further comprising an automated device that allows both filling and emptying of said compartments as well as sequential displacement of the multi-compartment setup.

23. A method of performing electrophoretic separation or purification of at least one charged and/or at least one neutral analyte from a solution by isoelectric focusing, comprising the steps of:
   providing an apparatus comprising: i) a series of at least two compartments having at least one wall portion composed of a chemical buffering means, said chemical buffering means forming a non-convective liquid junction interconnecting said at least two compartments and said chemical buffering means defining in each compartment of the series one of a fixed pH value and a pH gradient in a portion of the chemical buffering means contacting said analyte solution; ii) a thin layer fluidic connection between said at least two compartments allowing non-convective passage of solution from one compartment to another, said thin layer fluidic connection being one of a hole, a micro-channel, an array of holes or micro-channels, and a hollow passage; and iii) electrodes located in at least two of said compartments at extremities of the series;
   filling at least one of said compartments with said solution and filling any remaining compartments with another solution; and
   applying a potential difference between said electrodes located in said at least two compartments at the extremities of the series to force said charged analyte and/or undesired charged compounds present in said solution to move from one of said compartments to another or to the other of said compartments by virtue of the charge of said analyte and/or said undesired charged compounds at the pH value or in the pH range defined by the portion of the chemical buffering means contacting said analyte solution in each individual compartment of the series.

24. A method according to claim 23, wherein purified analytes are recovered directly in solution.

25. A method according to claim 23, wherein said chemical buffering means is used as a waste reservoir.

26. A method according to claim 23, wherein said at least one analyte is a biological compound.

27. A method according to claim 26, wherein said biological compound is selected form a group consisting of an organic compound, a protein, a protein derivative, and an isoform.

28. A method according to claim 27, wherein a plurality of analytes, each being a protein, is separated into proteins of the same isoelectric point and/or into individual proteins.

29. A method according to claim 23, wherein said at least one analyte is accumulated in the chemical buffering means.

30. A method according to claim 23, wherein said at least one analyte is accumulated in one of said compartments.

31. A method according to claim 23, wherein said analyte solution contains an organic solvent or is non-aqueous.

32. A method according to claim 23, wherein said analyte solution is renewed in at least one of said compartments.

33. A method according to claim 23, wherein said apparatus has a series of more than two compartments having one electrode in each compartment, and the potential difference between each pair of two adjacent electrodes is controlled.

34. A method according to claim 23, wherein the chemical buffering means is selected from a group consisting of a gel comprising immobilized buffering molecules, and a fluid supported on a support selected from a polymer matrix, a fritted glass, a porous membrane, a filter, and any combination thereof.

35. A method according to claim 34, wherein said support contains micro-holes through which charged analyte and/or undesired charged compounds can migrate upon application of an electric field.

36. A method according to claim 23, wherein buffering molecules are added to said analyte solution so as to enhance the buffering capacity of said chemical buffering means.

* * * * *

UNITED STATES PATENT AND TRADEMARK OFFICE
CERTIFICATE OF CORRECTION

| | | |
|---|---|---|
| PATENT NO. | : 7,390,389 B2 | Page 1 of 1 |
| APPLICATION NO. | : 10/486181 | |
| DATED | : June 24, 2008 | |
| INVENTOR(S) | : Rossier et al. | |

It is certified that error appears in the above-identified patent and that said Letters Patent is hereby corrected as shown below:

Column 2, line 33 "OffGel®) electrophoresis" should read --OffGel® electrophoresis--

Column 2, line 36 "an IPG gl)" should read --an IPG gel)--

Column 3, line 39 "allows difftision and" should read --allows diffusion and--

Column 11, line 60 "β-lactoglobin B" should read --β-lactoglobulin B--

Column 11, line 61 "β-lactoglobin B" should read --β-lactoglobulin B--

Column 12, line 9 "β-lactoglobin B" should read --β-lactoglobulin B--

Column 12, line 15 "β-lactoglobin B." should read --β-lactoglobulin B.--

Column 12, line 28 "β-lactoglobin B" should read --β-lactoglobulin B--

Column 12, line 33 "β-lactoglobin B" should read --β-lactoglobulin B--

Column 12, lines 36-37 "β-lactoglobin B" should read --β-lactoglobulin B--

Column 12, line 39 "β-lactoglobin" should read --β-lactoglobulin--

Column 13, line 7 "β-lactoglobin A" should read --β-lactoglobulin A--

Column 13, line 27 "β-lactoglobin" should read --β-lactoglobulin--

Column 14, line 25 "to the analy and" should read --to the analyte solution, and--

Signed and Sealed this

Fourteenth Day of October, 2008

JON W. DUDAS
*Director of the United States Patent and Trademark Office*